(12) United States Patent
De Leon Gatti et al.

(10) Patent No.: US 10,023,607 B2
(45) Date of Patent: Jul. 17, 2018

(54) PURIFICATION OF BIOLOGICAL CONJUGATES BY SIZE EXCLUSION CHROMATOGRAPHY

(71) Applicant: Abbott Laboratories, Abbott Park, IL (US)

(72) Inventors: Marcela De Leon Gatti, Arlington Heights, IL (US); Yingqing Huang, Mundelein, IL (US); David K. Schisla, Pleasant Prairie, WI (US); Lou-Hwa J. Sheu, Gurnee, IL (US); Christopher A. Tomas, Wauconda, IL (US)

(73) Assignee: Abbott Laboratories, Abbott Park, IL (US)

( * ) Notice: Subject to any disclaimer, the term of this patent is extended or adjusted under 35 U.S.C. 154(b) by 145 days.

(21) Appl. No.: 13/773,192

(22) Filed: Feb. 21, 2013

(65) Prior Publication Data

US 2014/0066605 A1 Mar. 6, 2014

Related U.S. Application Data

(63) Continuation of application No. 12/199,047, filed on Aug. 27, 2008.

(51) Int. Cl.

| | |
|---|---|
| *A61K 35/00* | (2006.01) |
| *C07K 16/00* | (2006.01) |
| *C12P 21/08* | (2006.01) |
| *C07K 1/00* | (2006.01) |
| *C07K 14/00* | (2006.01) |
| *C07K 17/00* | (2006.01) |
| *C07K 1/16* | (2006.01) |
| *C07K 1/34* | (2006.01) |
| *C07G 11/00* | (2006.01) |
| *C07H 17/08* | (2006.01) |
| *A61K 39/00* | (2006.01) |

(52) U.S. Cl.
CPC .......... *C07K 1/16* (2013.01); *C07K 1/34* (2013.01); *A61K 2039/505* (2013.01); *C07G 11/00* (2013.01); *C07H 17/08* (2013.01)

(58) Field of Classification Search
CPC ........... G01N 2030/02; G01N 2030/00; G01N 2001/2202; G01N 33/53; G01N 33/537; A61K 45/06; B01D 15/34
See application file for complete search history.

(56) References Cited

U.S. PATENT DOCUMENTS

| | | | |
|---|---|---|---|
| 2003/0017504 A1* | 1/2003 | Roberts et al. | ............... 435/7.1 |
| 2007/0172878 A1* | 7/2007 | Akhavan-Tafti et al. | ........ 435/6 |
| 2007/0253973 A1* | 11/2007 | Rosen et al. | ............... 424/189.1 |
| 2008/0242846 A1* | 10/2008 | DeFrees et al. | ............. 530/395 |
| 2009/0088336 A1* | 4/2009 | Burd et al. | ........................ 506/9 |
| 2014/0178386 A1* | 6/2014 | Urech | ....................... 424/135.1 |

FOREIGN PATENT DOCUMENTS

WO WO 2006/065867 A2 * 6/2006

OTHER PUBLICATIONS

Siiman et al. (Bioconjugate Chem., 1999; 10: 1090-1106).*
Abbott Diagnostics Divison, DFG83, Gel Permeation Chromatography by HPLC, Edition No. 011, Dec. 28, 2007, pp. 1-34.
Agar—Wikipedia, the free encyclopedia [online], [retrieved on Aug. 19, 2008]. Retrieved from the Internet: <URL: http://en.wikipedia.orglwiki/Agarose>.
Andrews P., "Estimation of the Molecular Weights of Proteins by Sephadex Gel-Filtration," Biochemical Journal, 1964, vol. 91 (2), pp. 222-233.
Bio-Rad Laboratories. Brochure [online]. Bio-Gel@ Polyacrylamide Gel Instruction Manual L1T174 Rev B [retrieved on Oct. 31, 2007] Retrieved from the Internet: URL: http://www.bio-rad.com/webmaster/pdfs/9154_Bio-Gel_P.pdf> pp. 1-21.
Bio-Rad Laboratories. Catalog [online]. Gel Filtration Standard Catalog #151-1901 [retrieved on Oct. 31, 2007] Retrieved from the Internet: : <URL: http://www.biorad.com.tw/cmc_upload/Literature/12697/MSLIT-102E.pdf> pp. 1-5.
Dextra—Wikipedia, the free encyclopedia [online], (retrieved on Aug. 19, 2008). Retrieved from the Internet: <URL: http://en.wikipedia.org/wiki/Dextran >.
Helpful Tips for Successful Chromatography, Phenomenex Technical Corner HPLC Factors Controlling Resolution, [online], [retrieved on Aug. 21, 2008]. Phenomenex, 2008 Retrieved from the Internet: <URL: http://www.phenomenex.com/resources/default.aspx"id=8565 >.

(Continued)

*Primary Examiner* — Gary B Nickol
*Assistant Examiner* — Lakia J Jackson-Tongue
(74) *Attorney, Agent, or Firm* — Melissa E. Kolom; Casimir Jones, S.C.

(57) ABSTRACT

A method for separating a biological conjugate from an aggregate. The molecular weight of the biological conjugate ranges from about 10 kDa to about 1000 kDa. In one embodiment, the method comprises the steps of:
(e) providing a mixture comprising the biological conjugate and the aggregate, wherein the biological conjugate has a molecular weight of from about 10 kDa to about 1000 kDa;
(f) providing a chromatography column containing a gel, wherein the gel comprises at least one polysaccharide;
(g) introducing the mixture of step (a) into the chromatography column;
(h) recovering the biological conjugate from the column.

13 Claims, 13 Drawing Sheets

(56) References Cited

OTHER PUBLICATIONS

Lake et al., Restek Pharmaceutical Article-Assaying Tetracyclines by HPLC, Developing a Simple, Rugged HPLC Assay for Tetracyclines (online), [retrieved on Aug. 21, 2008]. Retrieved from the Internet: <URL: http://www.restek.com/aoi_pharm_A003.asp>.

Pereira, et al., Use of Small Particles in Ultra High Pressure Liquid Chromatography, Thermo Electron Corporation [online], [retrieved on Feb. 2, 2009). Retrieved from the Internet: <URL: http://www.thermo.com/eThermo/CMA/PDFs/Product/productPDF_30724.pdf>.

Sephacryl S-100, S-200, S-300, S-400, S-500 High Resolution Instructions 52-2086-00 AK, [online], GE Healthcare Bio-Sciences AB, 2005 [retrieved on Feb. 19, 2009). Retrieved from the Internet: <URL: http://www5.gelifesciences.com/APTRIX/upp00919.nsf/content/ADAEB6631A0EE8F6C12570AF000DC820"OpenDocument&Path=Catalog&Hometitle=Catalog&entry=7&newrel&LinkParent=C1256FC4003AED40-0F96FF6249D1CACEC125701900490FBA_RelatedLinksNew>, pp. 5-11.

Silica gel—Wikipedia, the free encyclopedia [online], [retrieved on Aug. 19, 2008]. Retrieved from the Internet: <URL: http://en.wikipedia.org/wiki/Silica_gel >.

Skoog and West, Principles of Instrumental Analysis, Second Edition, Saunders College/Holt, Rinehart and Winston (Philadelphia, PA: 1980), 690-705.

Superdex 200 HR 10/30 Instructions 71/7059-00 Edition AE [online]. Amersham Pharmacia Biotech AB,1998 [retrieved on Feb. 19, 2009). Retrieved from the Internet: <URL: http://www.uga.edu/bff/pdfs/Superdex200_HR10-30 . PDF>, pp. 1-6.

Tosoh Bioscience LLC. TSK-GEL SW-type Columns for Protein Analysis and Isolation [online], [retrieved on Aug. 19, 2008]. Retrieved from the Internet: <URL: http://www.separations.us.tosohbioscience.com/ProductsPrinterFriendlyTemplate.aspx"N.>.

Using Bonded Phase Selectivity to Optimize High Throughput HPLC Separations, MAC-MOD Analytical, Inc.,Technical Report 03051TR [online], (retrieved on Feb. 3, 2009). Retrieved from the Internet: <URL: http://Www.macmod.com/tr/03051-tr.htm >.

Waters. Instruction Manual [online]. Waters 2695 Separations Module Quick Start Guide, 71500269503, Revision A. Milford, MA. [retrieved on Oct. 31, 2007] Retrieved from the Internet: (URL: http://www.meadowshplc.com/pdfs/2695_Separations_Module_Quick_Start_Guide.pdf), pp. 1-55.

\* cited by examiner

PURIFICATION OF BIOLOGICAL CONJUGATES BY SIZE EXCLUSION CHROMATOGRAPHY

BACKGROUND OF THE INVENTION

1. Field of the Invention

This invention relates to a method for purifying biological conjugates by means of size exclusion chromatography. More particularly, the invention relates to purifying a biological conjugate by means of a chromatography column, whereby there is a high degree of separation between a biological conjugate and an aggregate.

2. Discussion of the Art

An immunoassay is a test that uses complexes comprising antibodies and antigens to generate a detectable and measurable result. A complex comprising and antibody and an antigen is also known as an immuno-complex. Immunoassays are different from other types of laboratory tests, such as colorimetric tests, because most routine clinical chemistry tests utilize chemical reactions between a reagent (a solution of chemicals or other agents) and a biological sample from a patient to generate a test result. For the purpose of an immunoassay, an antibody or an antigen that is able to specifically bind to a target molecule of interest within a biological sample is cross-linked to a label, i.e., a molecule capable of being detected and used for measurement. Examples of a label include a radioactive compound, an enzyme that causes a change of color in a solution, fluorescent markers, a substance that produces light, such as, for example, a chemiluminescent material, and biotin.

Immunoassays utilize one or more selected antibodies or antigens to detect analytes of interest. An analyte is a substance, the concentration of which can be measured by a laboratory test. In immunoassay testing, the analyte can be either an antibody or an antigen. The analytes being measured can be substances that occur naturally in the body, such as, for example, a thyroid hormone). Alternatively, the analytes can be substances that the body produces but that are not typically present in the body, such as, for example, a cancer antigen. Still further, the analytes can be substances that do not naturally occur in the body, such as for example, a drug of abuse. Antibodies possess high specificity and affinity for a specific antigen. It is the specific binding of an antibody to an antigen that allows the detection of analytes by a variety of immunoassay techniques.

The most common format for an immunoassay is the noncompetitive assay format, which generally provides the highest levels of sensitivity and specificity and is typically used for the measurement of critical analytes, such as, for example, cardiac and hepatitis markers. This format is frequently referred to as the "sandwich" assay format, because the analyte is bound (sandwiched) between two highly specific antibody reagents, i.e., the capture antibody and the biological conjugate. A biological conjugate is an entity brought about by the linking of two or more molecules to form a complex that combines properties of its individual components. The reactive site for conjugation can include reactive sites of such molecules as amino acids, peptides, proteins, various sugars, nucleic acids, and oligonucleotides. A wide variety of reaction chemistries for forming biological conjugates can be employed to create such biological conjugates and are well known to those having ordinary skill in the art. Reactive groups that can be used to prepare biological conjugates include amines, thiols, carboxylates, hydroxyl, and aldehydes. In addition to the wide variety of reactive sites and chemical reactions that can be used to form biological conjugates, there is also a wide variety of cross-linking agents that most commonly include zero-length cross-linkers (e.g., 1-ethyl-3-(3-dimethylaminopropyl)carbodiimide hydrochloride), homobifunctinoal crosslinkers (e.g., N-hydroxysuccinimide ester), and heterobifunctional cross-linkers (e.g., succinimidyl-4-(N-maleimidomethyl)cyclohexane-1-carboxylate succinimide).

The resulting biological conjugate is typically purified after the conjugation reaction. Purification is performed to carried out to remove non-conjugated materials and/or to remove unwanted components, such as, for example, aggregated proteins and aggregated labels, referred to herein as aggregates. The removal of non-conjugated material and large aggregates can greatly improve the performance of an assay; for example, sensitivity can be improved, signal-to-noise ratios can be increased, and wash-cycle efficiency can be improved.

Chromatography is frequently used to purify biological conjugates. Chromatography is a technique wherein the components of a sample, carried by a liquid, are resolved on a stationary phase. While various types of chromatographic processes can be used to purify reaction mixtures containing biological conjugates, such as ion-exchange chromatography, the most common technique is Gel Permeation Chromatography (GPC), also known as size exclusion chromatography. Gel Permeation Chromatography is based on the selective permeation of soluble proteins through a column of particles of a particular size, which particles have pores of a known size. Proteins of a size larger than the pores will not enter the pores. Large proteins that do not enter the pores pass around the particles and are eluted in the void volume ($V_o$). Very small proteins and salts are retained within the particles until the total permeation volume ($V_t$) is reached. Proteins that elute between the void volume and the total permeation volume are resolved, based upon the size and shape of their molecules.

It would be desirable to develop a method for purifying a biological conjugate, which method would provide a consistent biological conjugate, consistency being based on size. It would also be desirable to develop a method for purifying a biological conjugate in which the biological conjugate is free from undesired chemical interactions. It would be further desirable to develop a method for purifying a biological conjugate, which method would be capable of resolving both high molecular weight materials and low molecular weight materials from the biological conjugate.

SUMMARY OF THE INVENTION

In one aspect, this invention provides a method for separating a biological conjugate from an aggregate. The molecular weight of the biological conjugate ranges from about 10 kDa to about 1000 kDa. In one embodiment, the method comprises the steps of:

(a) providing a mixture comprising the biological conjugate and the aggregate, wherein the molecular weight of the biological conjugate has a specified range of molecular weight, i.e., from about 10 kDA to about 1000 kDa, and preferably, has a specified range of molecular structures, e.g., globular;

(b) providing a chromatography column containing a gel, wherein the gel comprises at least one polysaccharide;

(c) introducing the mixture of step (a) into the chromatography column; and (d) recovering the biological conjugate from the column.

The biological conjugate comprises a specific binding member attached to a label. The aggregates differ from the biological conjugates in that fewer of the aggregates are retained in the pores of the gel on account of size, aggregates being larger in size than biological conjugates, with the result that the aggregates travel through the column faster than do the biological conjugates, thereby eluting before the biological conjugates. The chromatography column can separate the biological conjugates from the aggregates with a selectivity value of at least about 1.8, and preferably up to about 3.6. The loading volume of the chromatography column ranges from about 0.2% to about 15.4% of the volume of the column. The batch size ranges from about 50 mg to about 225 mg. The input ratio (volume of label to weight of specific binding member) ranges from about 0.5 µL of the label/mg of the specific binding member to about 6 µL of the label/mg of the specific binding member, wherein the concentration of the label is approximately 4 mg/mL.

BRIEF DISCUSSION OF THE DRAWINGS

Figure 4A:
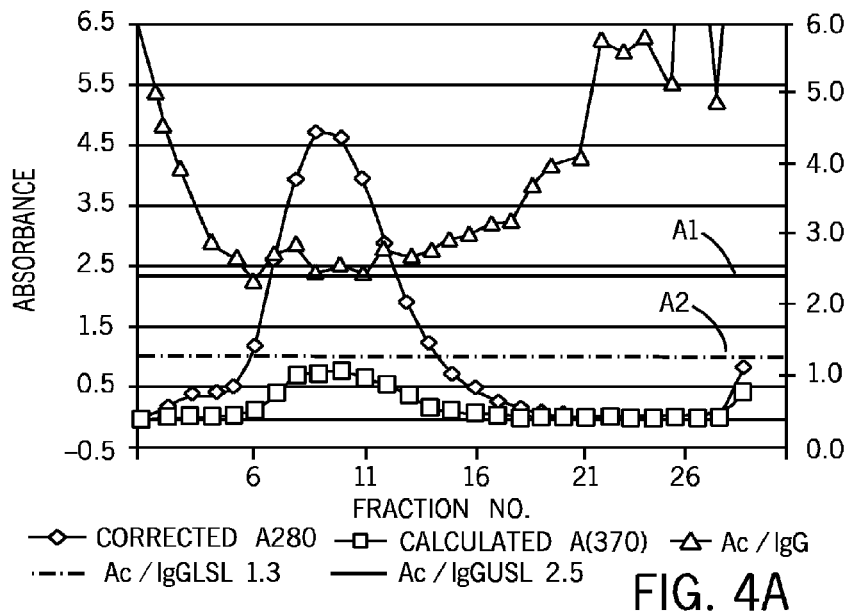
Figure 4B:
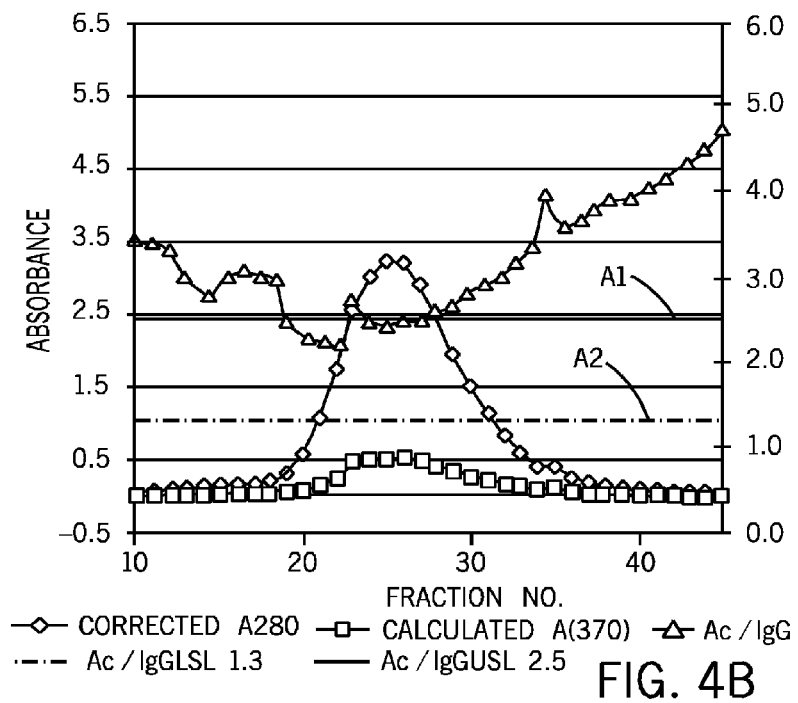
Figure 4C:
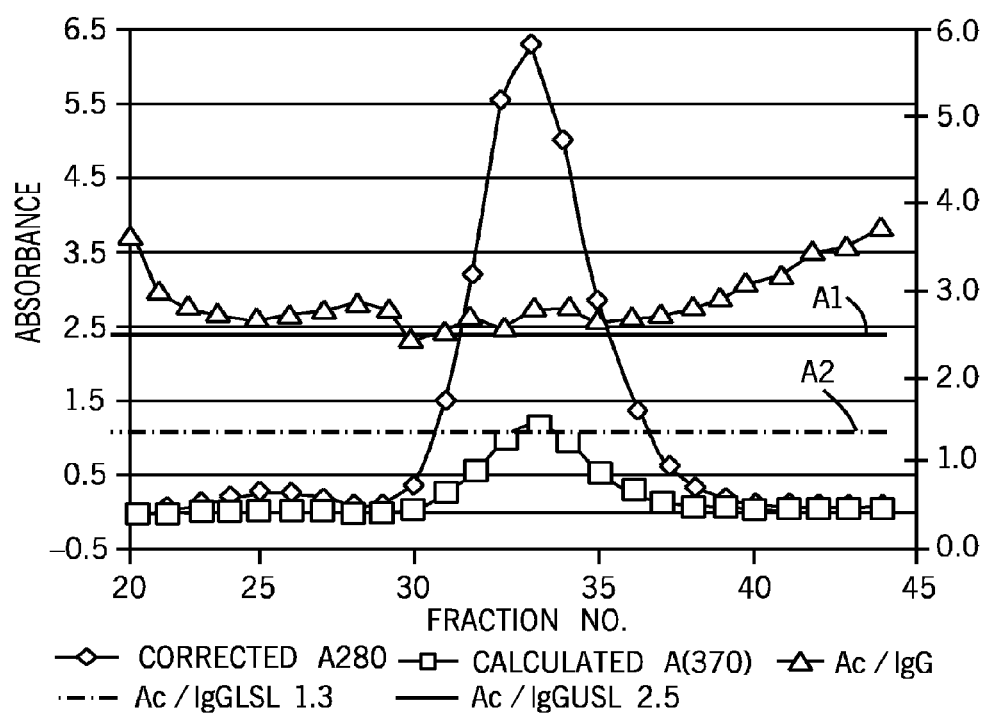
Figure 4F:
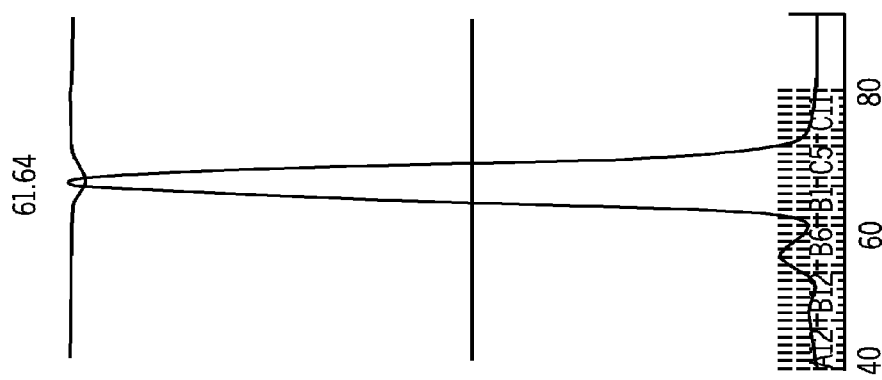
Figure 4E:
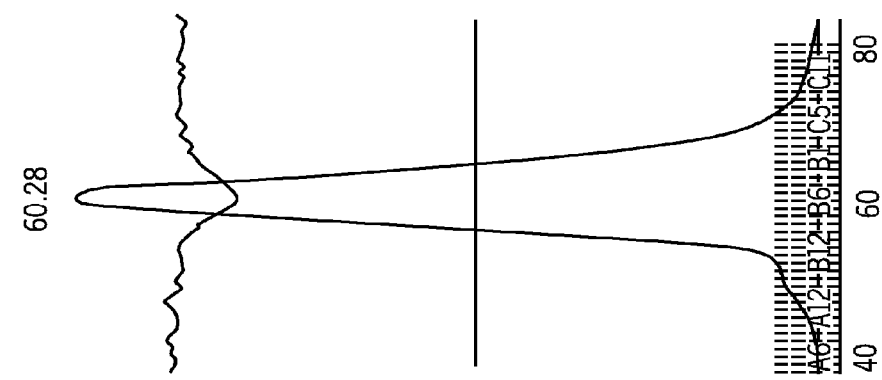
Figure 4D:
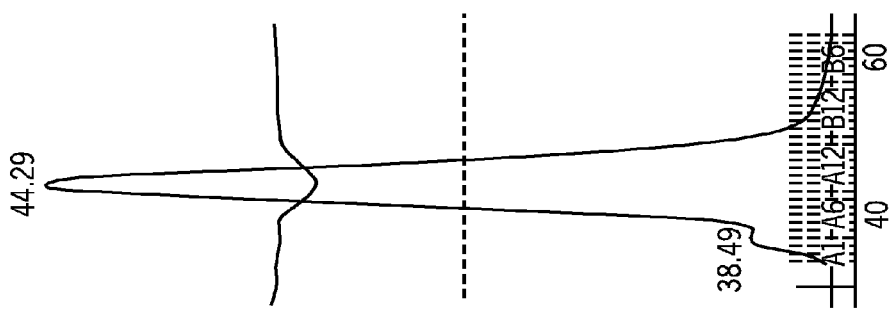

FIGS. 4A, 4B, 4C, 4D, 4E, and 4F are chromatograms illustrating the separation of a conjugate from an aggregate that elutes earlier. FIG. 4A is a chromatogram derived from a SEPHACRYL™ S-200 High Resolution gel filtration chromatography column; FIG. 4B is a chromatogram derived from a SEPHACRYL™ S-300 High Resolution gel filtration chromatography column; FIG. 4C is a chromatogram derived from a HILOAD™ 16/60 SUPERDEX™ 200 pg chromatography column. All three purifications were performed at a rate of flow of 1.0 mL/min. The chromatograms in FIGS. 4A, 4B, and 4C show absorbance as a function of the fraction number. FIG. 4D is a chromatogram derived from a SEPHACRYL™ S-200 High Resolution gel filtration chromatography column; FIG. 4E is a chromatogram derived from a SEPHACRYL™ S-300 High Resolution gel filtration chromatography column; FIG. 4F is a chromatogram derived from a HILOAD™ 16/60 SUPERDEX™ 200 pg chromatography column. All three purifications were performed at a rate of flow of 1.0 mL/min. The chromatograms in FIGS. 4D, 4E, and 4F show absorbance as a function of time.

Figure 5A:
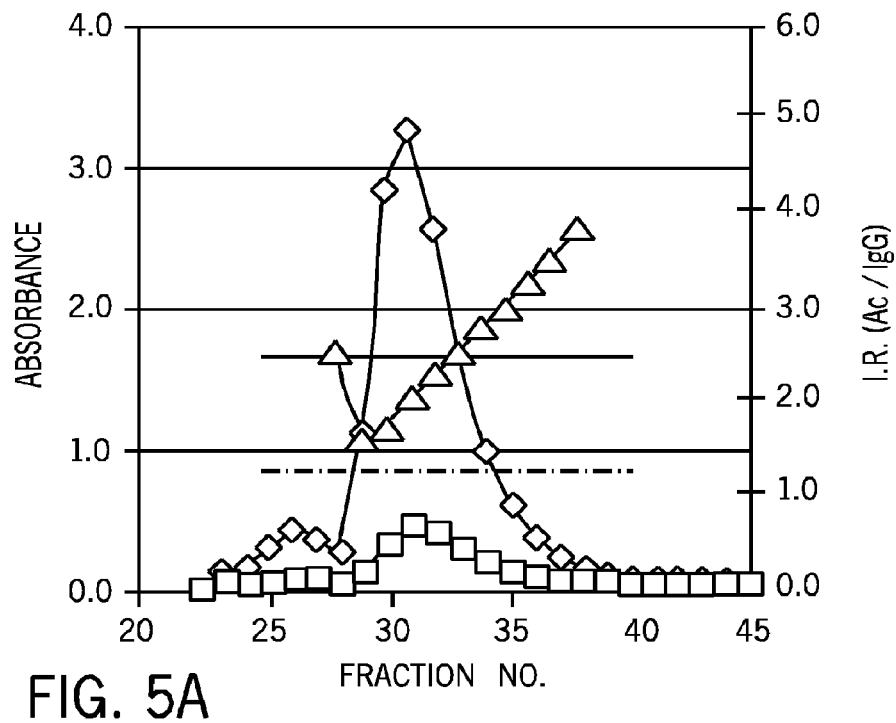
Figure 5B:
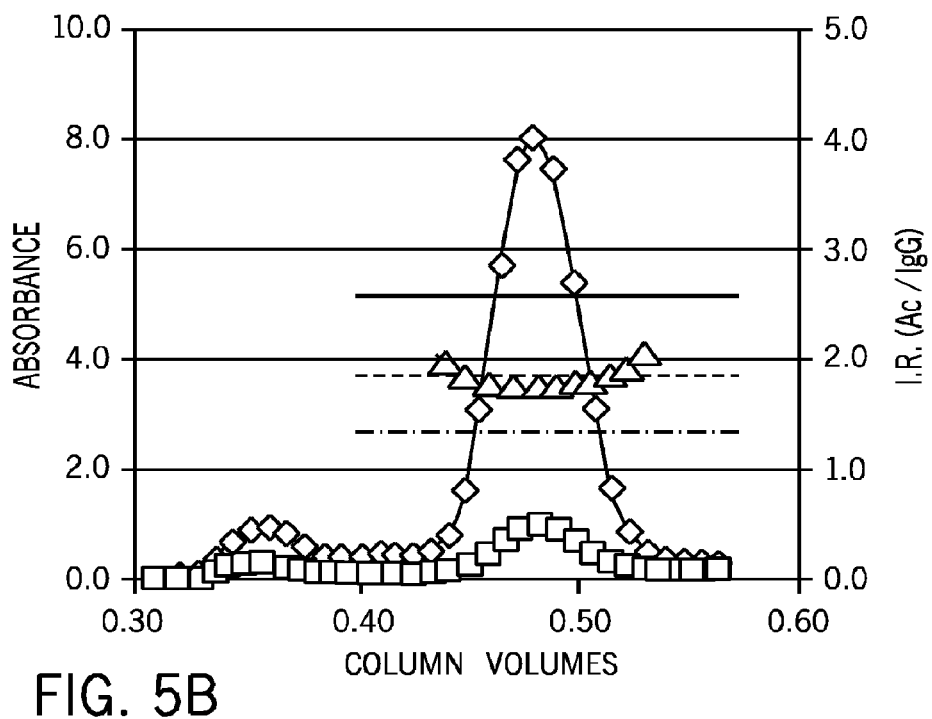

FIG. 5A is a representative chromatogram profile of a biological conjugate containing anti-biotin antibody purified on a silica-based chromatography column. FIG. 5B is a representative chromatogram profile of a biological conjugate containing anti-biotin antibody purified on a HILOAD™ 16/60 SUPERDEX™ 200 pg chromatography column. In FIGS. 5A and 5B, diamonds indicate absorbance at a wavelength of 280 nm; squares indicate absorbance at a wavelength of 370 nm; triangles indicate Ac/IgG IR values. The solid horizontal lines indicate lower and upper Ac/IgG IR values for pooling; the dashed horizontal line indicates the target Ac/IgG IR value, which is approximately 1.8.

Figure 6A:
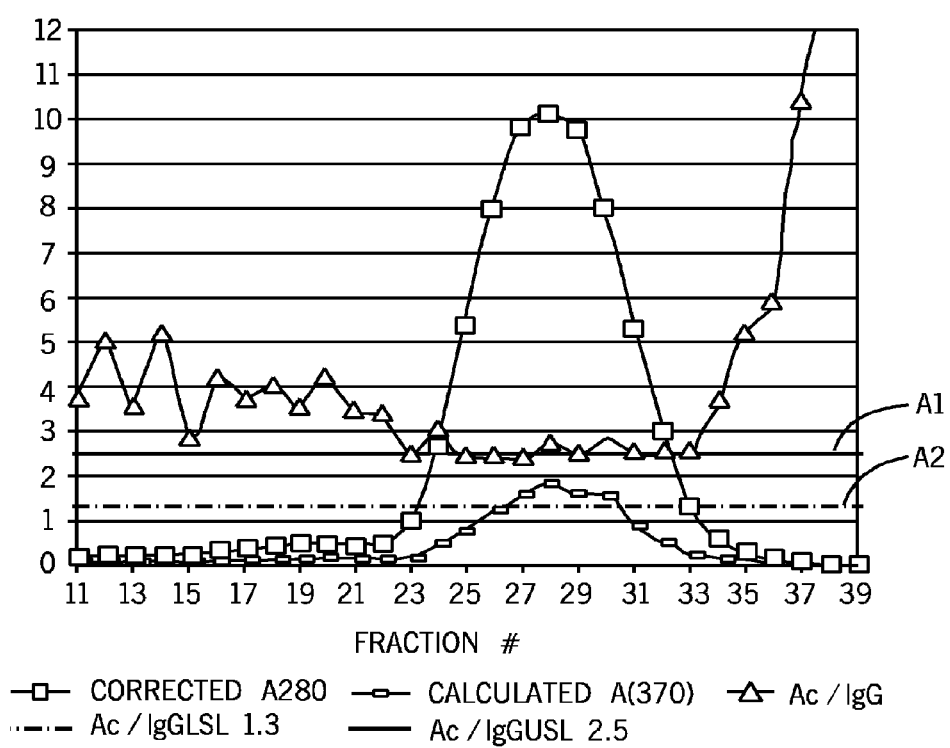
Figure 6B:
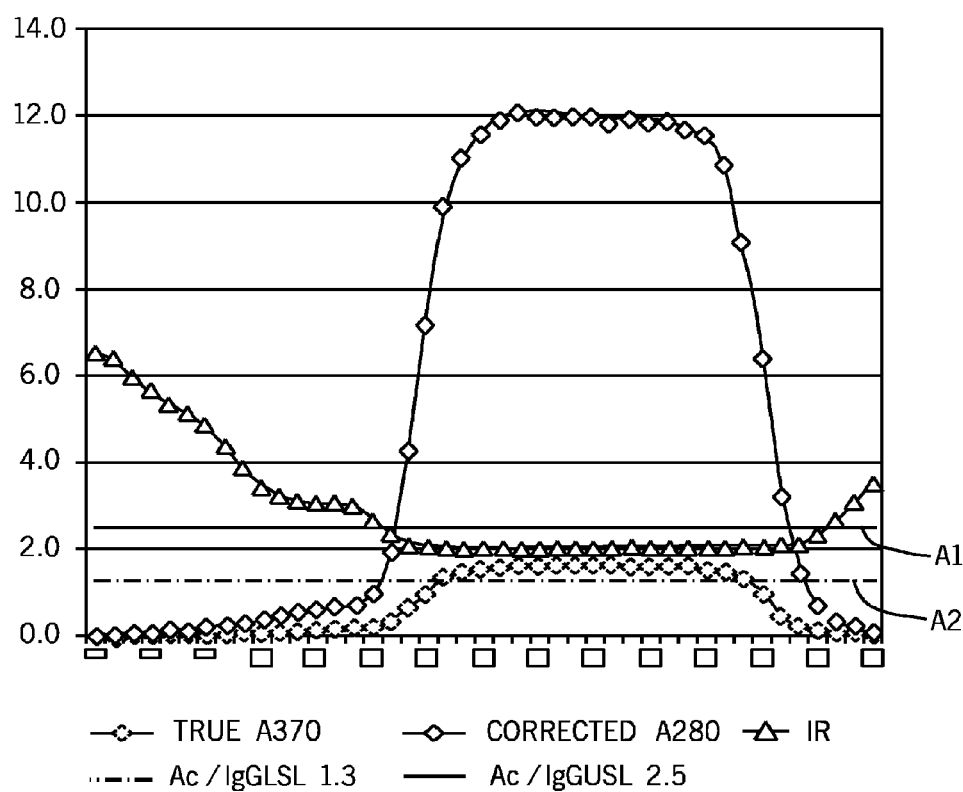
Figure 6C:
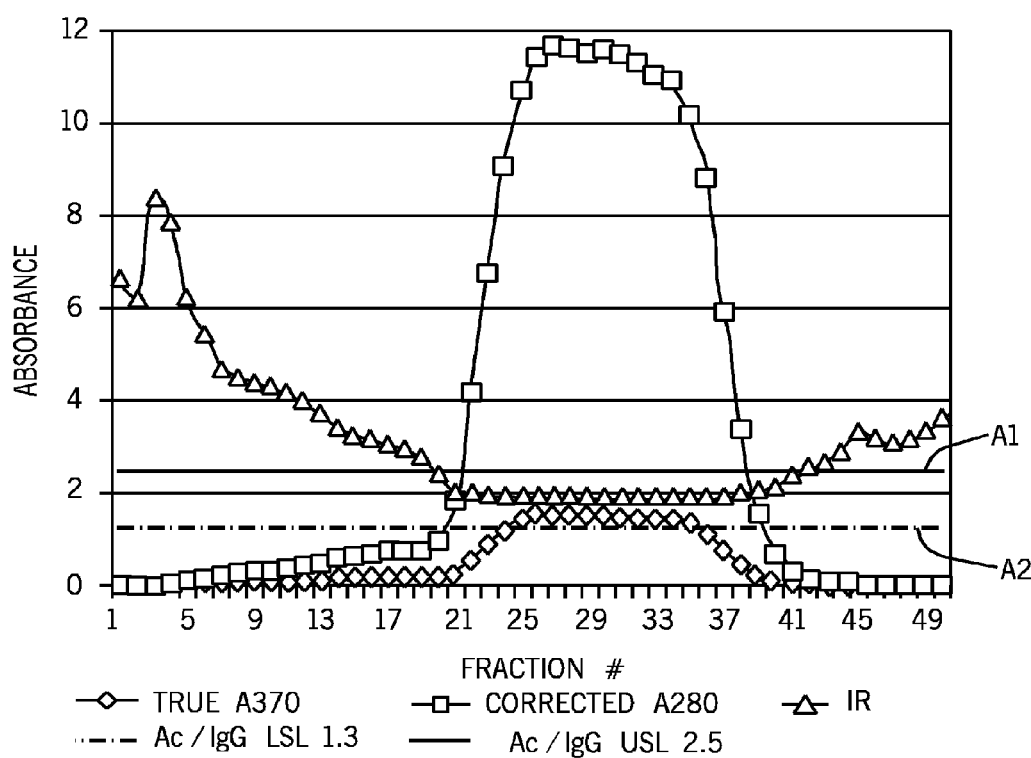
Figure 6D:
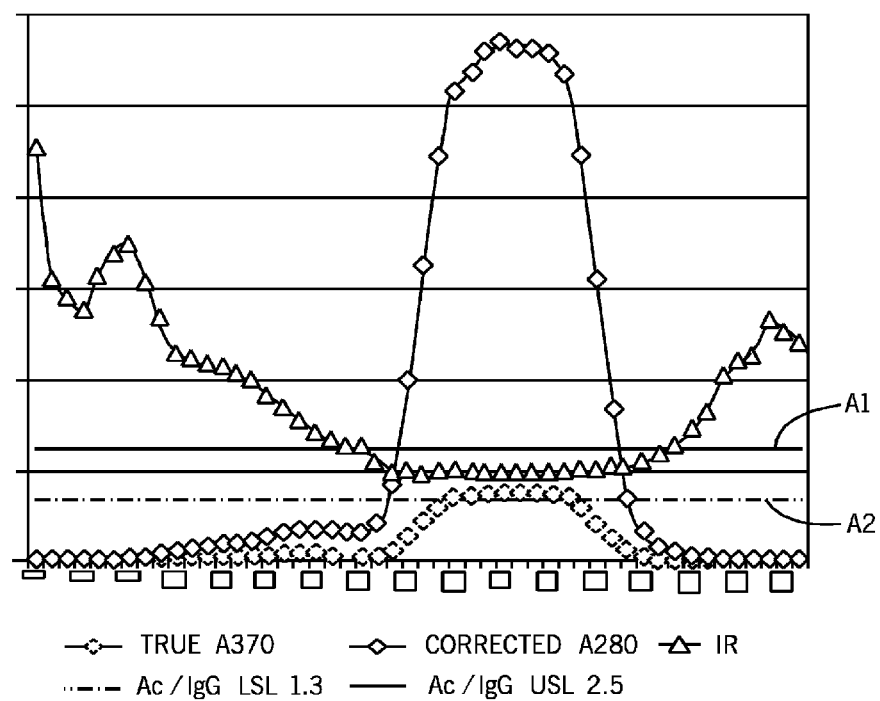

FIGS. 6A, 6B, 6C, and 6D are chromatograms illustrating the effect of various loadings of the HILOAD™ 16/60 SUPERDEX™ 200 pg chromatography column. FIG. 6A illustrates the effect of a loading of 5%. FIG. 6B illustrates the effect of a loading of 15.4%. FIG. 6C illustrates the effect of a loading of 12.5%. FIG. 6D illustrates the effect of a loading of 10%.

Figure 7:
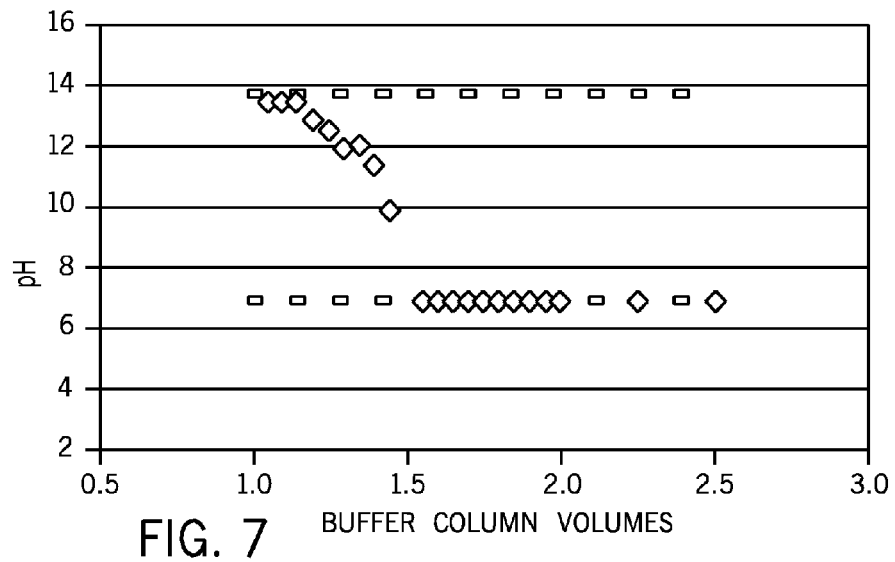

FIG. 7 illustrates the pH profile of the column eluent after a clean in place procedure using 0.5 N sodium hydroxide (NaOH). The upper dashed line represents the pH of 0.5 N NaOH (13.7), while the lower dashed line represents the pH of the phosphate buffered saline (PBS) buffer (7.0).

Figure 8:
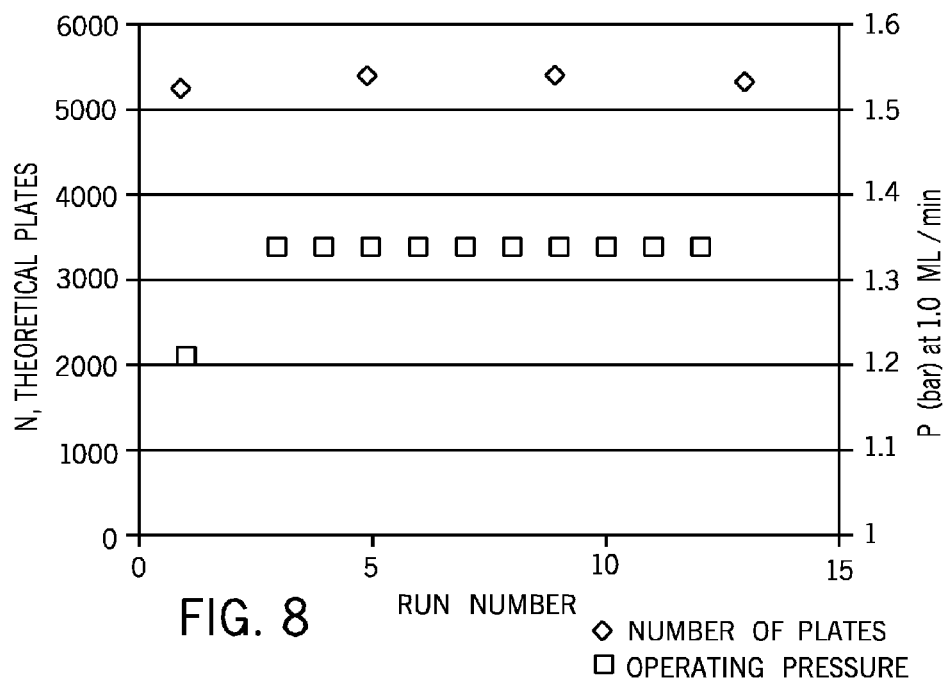

FIG. 8 illustrates the number of theoretical plates of a chromatography column and the operating pressure over the course of thirteen (13) anti-biotin conjugates [?] by utilizing a clean in place procedure.

Figure 9:
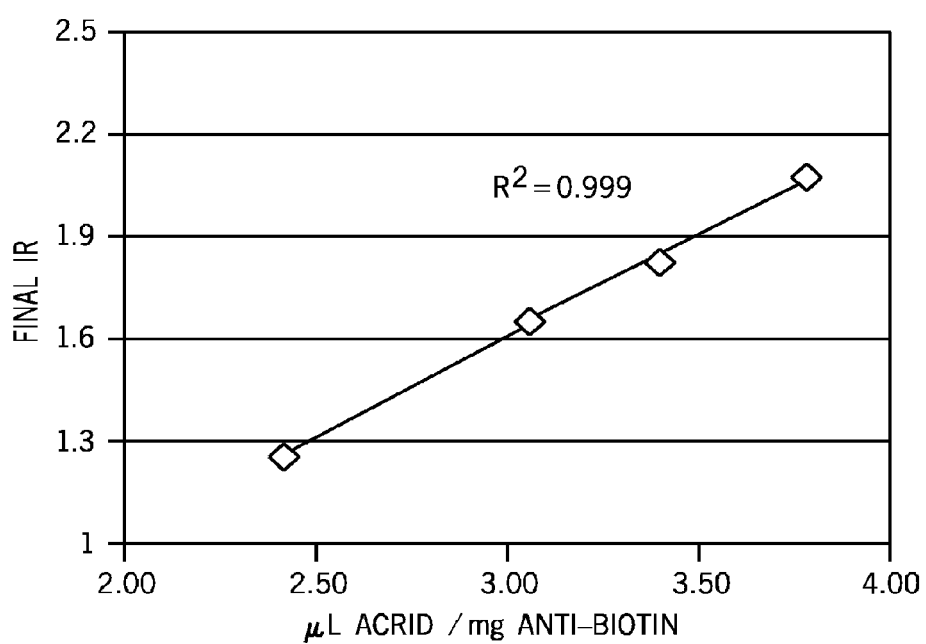

FIG. 9 illustrates the correlation between the final Ac/IgG IR values of the biological conjugates purified on a HILOAD™ 16/60 SUPERDEX™ 200 pg column with the input ratio of acridinium to anti-biotin antibody.

DETAILED DESCRIPTION

As used herein, the terms and expressions "conjugate", "biological conjugate", and the like, mean a specific binding member attached to a label. As used herein, the expression "specific binding member" means an antigen or an antibody that binds to the specific item (i.e., antigen or antibody) to which it is supposed to bind without binding to a similar item (i.e., antigen or antibody) to which it is not supposed to bind. As used herein, the expression "conjugate containing an anti-biotin antibody" means a conjugate containing an antibody that specifically binds to biotin.

As used herein, the term "label" means a moiety attached to an antibody or an antigen to render the reaction between the antibody and the antigen detectable. A label is capable of producing a signal that is detectable by visual or instrumental means. Various labels suitable for use in this invention include signal-producing substances such as chromogens, fluorescent compounds, chemiluminescent compounds, and the like. Representative examples of labels suitable for this invention include moieties that produce light, e.g., acridinium compounds, and moieties that produce fluorescence, e.g., fluorescein.

The expressions "sample", "test sample", and the like, as used herein, refer to a material suspected of containing an analyte. The test sample can be used directly as obtained from the source or following a pretreatment to modify the character of the sample. The test sample can be derived from any biological source, such as a physiological fluid, such as, for example, blood, saliva, ocular lens fluid, cerebral spinal fluid, sweat, urine, milk, ascites fluid, synovial fluid, peritoneal fluid, amniotic fluid, and the like. The test sample can be pretreated prior to use, such as preparing plasma from blood, diluting viscous fluids, and the like. Methods of pretreatment can involve filtration, distillation, extraction, concentration, inactivation of interfering components, the addition of reagents, and the like.

As used herein, the term "anti-biotin antibody" means an antibody to biotin. As used herein, the expression "incorporation ratio" means the ratio of the label to the specific binding member in a biological conjugate. As used herein, the expression "overcoat buffer" means a solution containing buffer and a non-specific protein, e.g., bovine serum albumin, used to treat microparticles after the microparticles are coated with a specific protein, such as an antibody.

As used herein, the term "column" refers to a column used in a chromatographic process. As used herein, the expression "bed volume" means the volume of the chromatographic medium in a column.

As used herein, the terms "load", "loaded", and the like, refer to injecting a specified volume of a reaction mixture for preparing a biological conjugate into a column for the purpose of separating the biological conjugate from the other components of the reaction mixture. As used herein, the expression "column loading volume" means the volume of reaction mixture injected into the column. The expression "maximum column loading volume" means the maximum volume of reaction mixture that can be injected into a column. As used herein, the expression "batch size" means the scale at which the biological conjugate is manufactured. The expression "maximum batch size" means the maximum scale at which the biological conjugate can be manufactured; the expression "minimum batch size" means the minimum scale at which the biological conjugate can be manufactured.

As used herein, the expression "theoretical plate" refers to the theoretical efficiency of a column. Equilibrium does not exist in any part of the column. The lack of equilibrium arises from the dynamic nature of the column as the mobile phase is continually flowing past the stationary phase. The solute does not spend sufficient time at any point in the column for equilibrium to be achieved. The column is considered to be divided into a number of theoretical plates and each is allotted a finite height (or length) that will allow the solute sufficient theoretical dwell-time for equilibrium to take place. It is clear that the faster the equilibrium, the smaller the theoretical plate, and the more theoretical plates there will be in the column. Thus, the more efficient column has more theoretical plates. Greater efficiency results in better resolution and better peak separation. The relationship between theoretical plate height, number of theoretical plates, and column length is [column length=theoretical plate height×number of theoretical plates].

As used herein, the terms "fraction", "fractionation", and the like, refer to a separation process in which a certain quantity of a mixture (solid, liquid, solute or suspension) is divided up in a number of smaller quantities (fractions) in which the composition changes according to a gradient. Fractions are collected based on differences in a specific property of the individual components. A common trait in fractionations is the need to find an optimum between the amount of fractions collected and the desired purity of each fraction. The expression "fractionation range" means the range of molecular weights that a chromatographic medium can separate optimally.

As used herein, the terms "pool", "pooling", and the like, refer to a grouping or consolidation of fractions in order to achieve a specified level of purity of the composition collected.

As used herein, the term "aggregate" means material having high molecular weight, such as, for example, equal to or greater than two times the weight of a single molecule of the biological conjugate.

As used herein, the term "Ac/IgG IR" means the incorporation ratio of the label, e.g., the acridinium moiety, in the biological conjugate to the specific binding member, e.g., anti-biotin antibody moiety, in the biological conjugate.

As used herein, the expression "input ratio" means the ratio of the label, e.g., acridinium, to the specific binding member, e.g., anti-biotin antibody, introduced into the reaction mixture for preparing a biological conjugate.

As used herein, the expression "stationary phase" means beads of a porous polymeric material that readily absorbs water (and in some instances, other solvents) and swells as a consequence. The resulting solid contains a large volume of solvent held in the interstices of the polymeric network. As used herein, the expression "mobile phase" means the solvent that runs through a liquid chromatographic instrument.

As used herein, the expression "globular protein" means a protein have a spherical structure.

General details on the operation of a GPC-HPLC column can be found in Skoog and West, PRINCIPLES OF INSTRUMENTAL ANALYSIS, Second Edition, Saunders College/Holt, Rinehart and Winston (Philadelphia, Pa.; 1980), pages 690-705, incorporated herein by reference. Additional details relating to the HILOAD™ 16/60 SUPERDEX™ 200 pg gel filtration chromatography column and the HILOAD™ 26/60 SUPERDEX™ 200 pg gel filtration chromatography column are described in GE Healthcare, Instructions 71-5020-20AF High Performance Columns, HILOAD™ 16/60 and 26/60 SUPERDEX™ 30 prep grade, HILOAD™ 16/60 and 26/60 SUPERDEX™ 75 prep grade, HILOAD™ 16/60 and 26/60 SUPERDEX™ 200 prep grade, General Electric Company 2005, incorporated herein by reference. The SEPHACRYL™ S-200 High Resolution gel filtration chromatography column and the SEPHACRYL™ S-3200 High Resolution gel filtration chromatography column are described in GE Healthcare, Instructions 52-2086-00 AK 5, SEPHACRYL™ S-100, S-200, S-300, S-400, S-500 High Resolution, General Electric Company 2005, incorporated herein by reference.

The separation of the biological conjugate from the aggregate is difficult because the molecular size of each of these entities is of the same order of magnitude. It has been discovered that HILOAD™ 16/60 SUPERDEX™ 200 pg column and the HILOAD™ 26/60 SUPERDEX™ 200 pg column can be used to satisfactorily separate the biological conjugate from the aggregate. The biological conjugate prepared by a fully scaled-up process can be purified using a HILOAD™ 26/60 SUPERDEX™ 200 pg column. As used herein, "fully scaled-up" means the maximum size of a batch in which the biological conjugate is expected to be manufactured. To maintain the percent of column loading below 15.4% on a HILOAD™ 26/60 SUPERDEX™ 200 pg column, the final volume of the biological conjugate must be less than about 49.0 mL (i.e., final volume of the conjugate is equal to the volume of the column of about 320 mL multiplied by the maximum value of the column loading of about 0.154). In other words, the maximum column load is equal to the largest volume of liquid that can be introduced into the column. Using this value of 15.4% column loading as an upper boundary, the theoretical maximum batch size supported by the characterization data can be calculated to be 225 mg. The actual upper limit of batch size is preferably set 75 mg below the theoretical upper limit.

Selectivity is a component of the resolution equation $$R = 1/4\underbrace{\left(\frac{\alpha-1}{\alpha}\right)}_{Selectivity} \underbrace{\left(\sqrt{N}\right)}_{Efficiency} \underbrace{\left(\frac{\kappa'}{1+\kappa'}\right)}_{Capacity}$$

where
$R_s$ represents resolution
$\alpha$ represents selectivity
N represents efficiency
$\kappa'$ represents retention factor The resolution equation and the components thereof are discussed in greater detail in Skoog and West, PRINCIPLES OF INSTRUMENTAL ANALYSIS, Saunders College/Holt, Rinehart and Winston (1980), pages 667-686, incorporated herein by reference. Other references that discuss the resolution equation and components thereof include Andrews, P., Estimation of the Molecular weights of Proteins by Sephadex Gel-Filtration, Biochem. J. (1964) 91, 222; Helpful Tips for Successful Chromatography, Phenomenex Technical Corner HPLC Factors Controlling Resolution, Phenomenex, 2008, available on the world wide web at the Phenomenex website; Developing a Simple, Rugged HPLC Assay for Tetracyclines, Restek Pharmaceutical Article--Assaying Tetracyclines by HPLC, available on the world wide web at the Restek website; MAC-MOD Analytical, Inc., Technical Report 03051 TR, available on the world wide web at the MAC-MOD website; and L. Pereira, et al., Use of Small Particles in Ultra High pressure Liquid Chromatography, Thermoelectron Corporation, available on the world wide web at the Thermoelectron website, all of which references are incorporated herein by reference. The method described herein can achieve a selectivity of at least about 1.8, and preferably from about 1.8 to about 3.6.

The range of batch sizes for a HILOAD™ 26/60 SUPERDEX™ 200 pg column can be set at 50 mg to 150 mg of the biological conjugate. The minimum batch size can be set equal to a column loading volume of approximately 2%. This column loading volume is equal to that used in the selection of the HILOAD™ 26/60 SUPERDEX™ 200 pg column, which provides excellent separation. At the maximum batch size, the highest percent of loading occurs when the anti-biotin antibody is at its lowest concentration, i.e., 7.0 mg/mL, which condition requires the largest volume of liquid capable of being introduced into the column. At a batch size of 150 mg, the maximum column loading volume is 32.7 mL. This value is equivalent to a 10.3% column loading volume on a HILOAD™ 26/60 SUPERDEX™ 200 pg column, and is approximately two-thirds (66.9%) the maximum column loading volume shown to be effective. A fully scaled-up run at the maximum batch size can be carried out on a HILOAD™ 26/60 SUPERDEX™ 200 pg column. A scaled-up run at the maximum batch size can also be carried out on a HILOAD™ 16/60 SUPERDEX™ 200 pg column. Yields of biological conjugate, Ac/IgG IR values, and assay performance will be acceptable over the range of batch sizes of 50 mg to 150 mg.

The following non-limiting examples further illustrate the invention described herein.

EXAMPLES

Figure 1A:
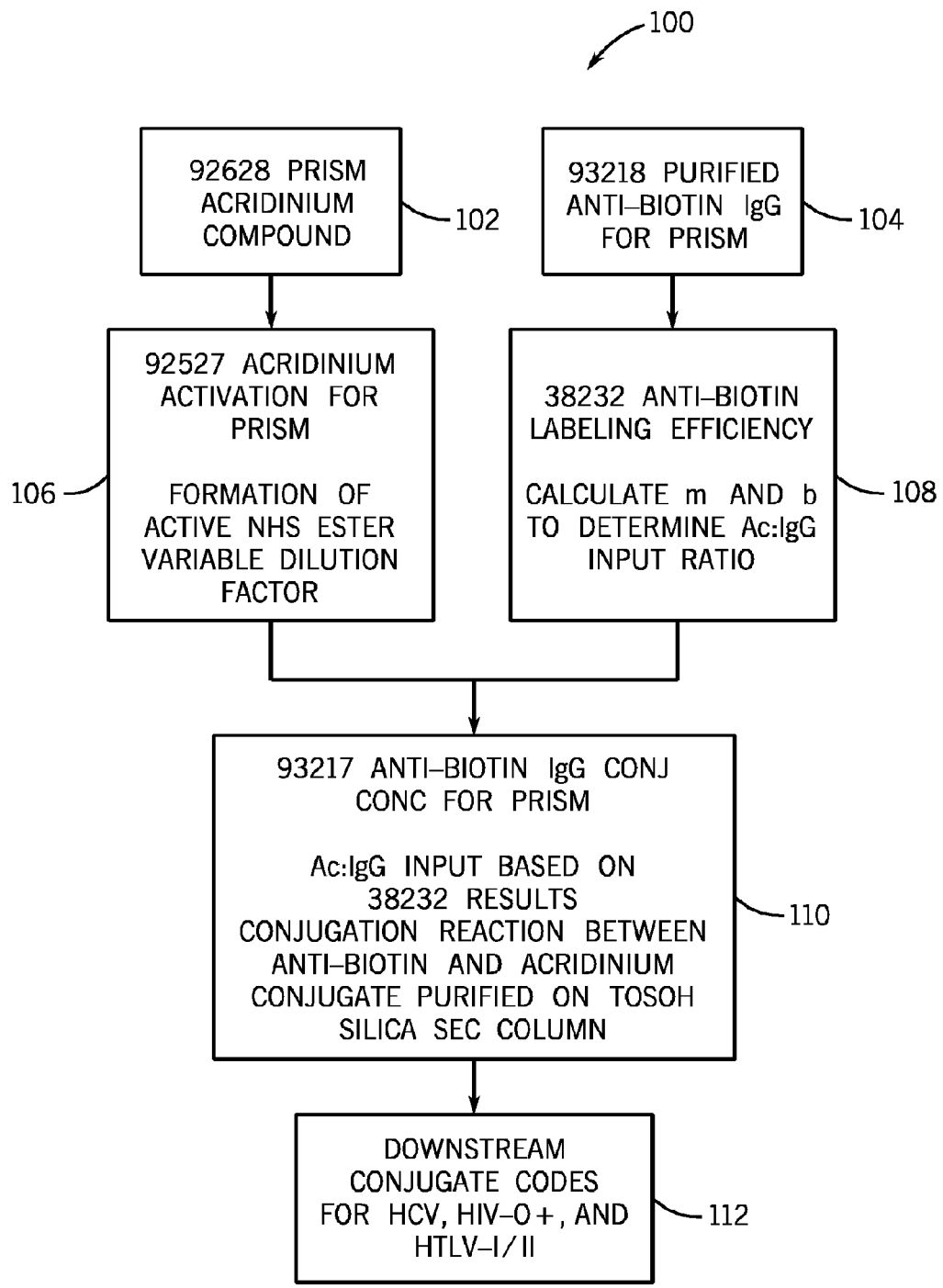
FIG. 1A is a process flow diagram illustrating a process currently used for manufacturing a biological conjugate containing an anti-biotin antibody.
Figure 1B:
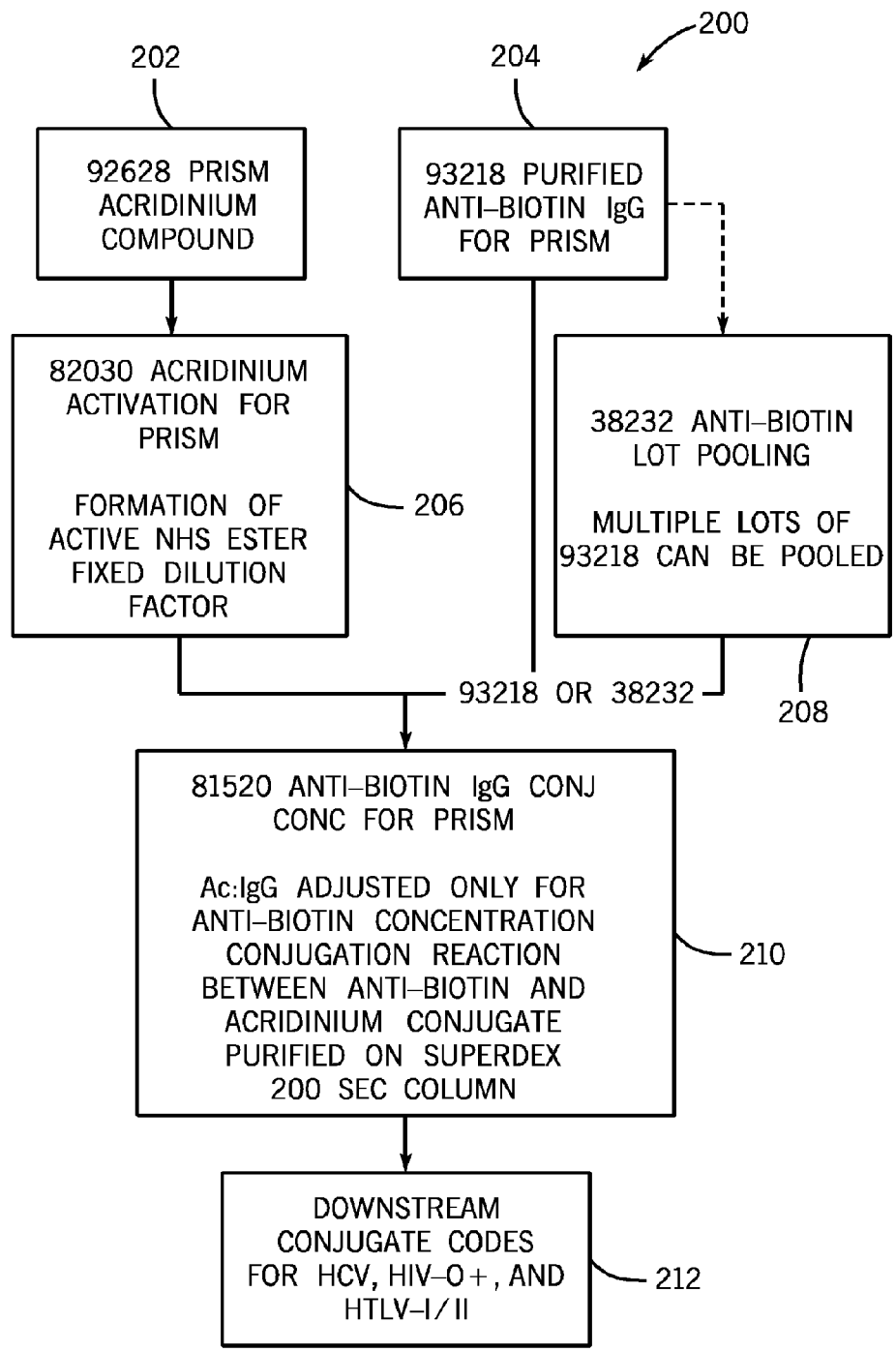
FIG. 1B is a process flow diagram illustrating the process described herein for concentrating a biological conjugate containing an anti-biotin antibody.

A biological conjugate suitable for use with the PRISM® immunoassay analyzer can be prepared with anti-biotin antibody as the specific binding member and activated acridinium as the label. FIG. 1A illustrates the steps for preparing the biological conjugate according to a method currently being used. FIG. 1B illustrates the steps for preparing the biological conjugate according to the method described herein. The current method 100 for preparing the biological conjugate involves the steps of:
  (a) providing an acridinium compound (step 102);
  (b) providing a purified anti-biotin antibody (step 104);
  (c) activating the acridinium compound (step 106);
  (d) determining the labeling efficiency for the anti-biotin antibody (step 108);
  (e) carrying out the conjugation reaction between the anti-biotin antibody and the activated acridinium compound based on the determination in step (d), and purifying the biological conjugate on a silica-based size exclusion chromatography column (step 110); and
  (f) providing the code for the assay (step 112).

The expression "labeling efficiency refers to the quantity of acridinium molecules that react to form the biological conjugate as a percentage of the total number of acridinium molecules introduced into the reaction. The symbol "m" represents the slope of the line that represents the incorporation ratio as a function of the input ratio. The symbol "b" represents the intercept of the line that represents the incorporation ratio as a function of the input ratio. When this line is determined by means of the preparation of the biological conjugate on a small scale, the line can be used to estimate the optimal input ratio for the desired incorporation ratio. In step 106, the dilution factor can be variable.

The method 200 for preparing the biological conjugate according to the method described herein involves the steps of:
  (a) providing an acridinium compound (step 202);
  (b) providing a purified anti-biotin antibody (step 204);
  (c) activating the acridinium compound (step 206);
  (d) optionally determining whether a plurality of lots of purified anti-biotin antibodies should be pooled (step 208);
  (e) carrying out the conjugation reaction between the purified anti-biotin antibody and the activated acridinium compound or the pooled lots of purified anti-biotin antibody and the activated acridinium compound, if it is decided that lots of purified anti-biotin antibodies should be pooled, and purifying the biological conjugate on a polysaccharide based size exclusion chromatography column (step 210); and
  (f) providing the code for the assay (step 212).

In step 206, the dilution factor is fixed. In the assay protocol in FIG. 1B, a purified anti-biotin antibody can be used (step 204), or, in the alternative, a plurality of lots of purified anti-biotin antibody can be pooled (step 206) and then used in the reaction for forming the biological conjugate.

Figure 2:
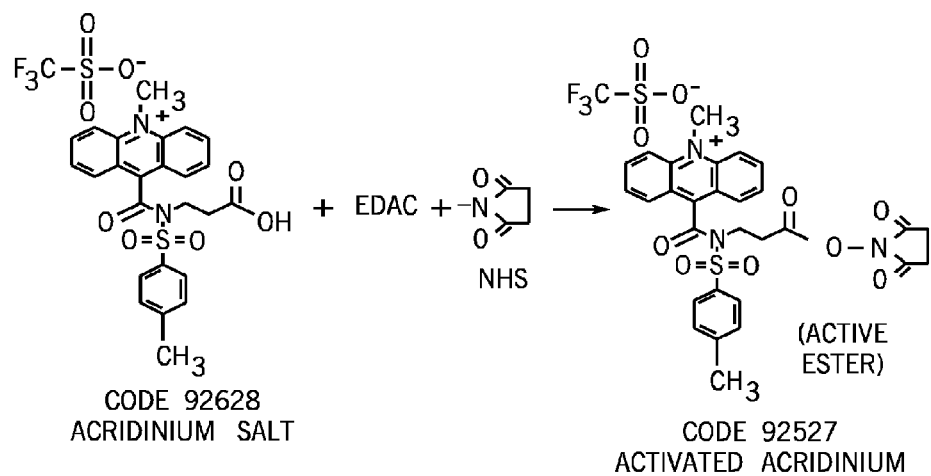
FIG. 2 is a diagram illustrating a process for activating acridinium showing conversion of the acridinium trifluoromethanesulfonate to the activated acridinium N-hydroxysuccinimide ester.
Figure 3:
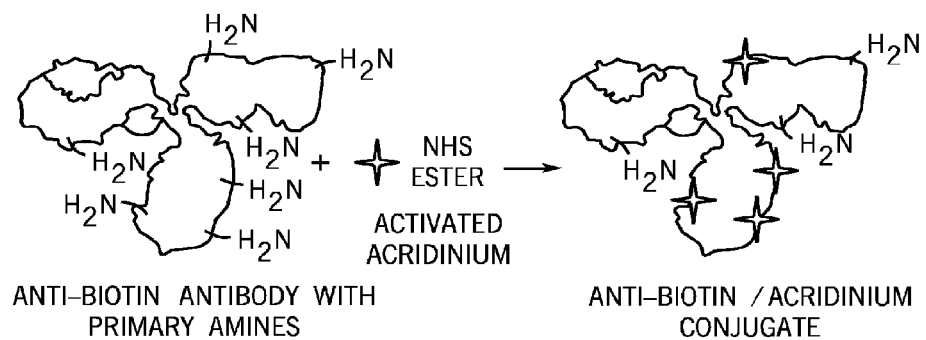
FIG. 3 is a diagram illustrating the conjugation reaction between an anti-biotin antibody and an activated acridinium N-hydroxysuccinimide ester.

The acridinium used in the illustrated conjugation process is converted to an activated acridinium molecule by means of N-hydroxysuccinimide ester before being used in the conjugation process, as shown in FIG. 2. EDAC is 1-ethyl-3-(3-dimethylaminopropyl)carbodiimide hydrochloride. The N-hydroxysuccinimide group on the activated acridinium molecule reacts with the free amine groups on the target antibody molecule (anti-biotin antibody), as shown in FIG. 3. FIG. 3 illustrates the conjugation reaction between the anti-biotin antibody and the activated acridinium N-hydroxysuccinimide ester group. It should be noted that the antibody having amine groups is shown for illustrative purposes only and is not based on known structural information.

The equipment, reagents, and materials used for the process characterization studies are listed below in TABLE 1 and in the List of Reagents. Stir plates, pH meters, balances, and pipettes are not included in the list of equipment.

TABLE 1

| Item | Source |
|---|---|
| Pharmacia Pump P-500 | Pharmacia (Amersham Biosciences, United Kingdom) |
| Pharmacia Optical Unit UV-1 with HR-10 Flow Cell | Pharmacia (Amersham Biosciences, United Kingdom) |

TABLE 1-continued

| Item | Source |
|---|---|
| Pharmacia FRAC-100R Fraction Collector | Pharmacia (Amersham Biosciences, United Kingdom) |
| Pharmacia Unicorn Controller | Pharmacia (Amersham Biosciences, United Kingdom) |
| Computer connected to Unicorn Controller | Pharmacia (Amersham Biosciences, United Kingdom) |
| Shimadzu UV-1610PC Spectrophotometer | Shimadzu, Kyoto Japan |
| Waters 600 Controller Model Code 6CE with Pump Model Code 60F | Waters Corporation, Milford, MA |
| Waters 2487 Dual Wavelength Absorbance Detector | Waters Corporation, Milford, MA |
| Waters In-Line Degasser AF | Waters Corporation, Milford, MA |
| Waters Column Selector | Waters Corporation, Milford, MA |
| Waters Fraction Collector III | Waters Corporation, Milford, MA |
| Beckman DU650 Spectrophotometer | Beckman Coulter, Inc., Fullerton, CA |
| HILOAD ™ 16/60 SUPERDEX ™ 200 pg | Amersham Biosciences, United Kingdom (GE Healthcare) |
| HILOAD ™ 26/60 SUPERDEX ™ 200 pg | Amersham Biosciences, United Kingdom (GE Healthcare) |

The item HILOAD™ 26/60 SUPERDEX™ 200 pg was used in EXAMPLE 4. The item HILOAD™ 16/60 SUPERDEX™ 200 pg was used in EXAMPLES 1, 2, 3, 5, 6, 7, and 8.

LIST OF REAGENTS

| Reagent |
|---|
| Purified anti-biotin antibody (IgG antibody) |
| Pooled anti-biotin antibody (IgG antibody) |
| Activated acridinium for PRISM ® diagnostic analyzer |
| Dialysis buffer (pH = 8) |
| Sodium azide |
| ARCH conjugate column buffer |
| Sodium phosphate monobasic |
| Sodium phosphate dibasic |
| Sodium chloride |
| 1N NaOH |
| 1N HCl |
| CHAPS |
| HPLC grade acetone (Sigma-Aldrich) |

Example 1

This example illustrates an arrangement for screening columns to determine whether a commercially available column is satisfactory for the desired degree of separation of the biological conjugate from the aggregate. In order to scale up the 15 preparation of the biological conjugate comprising the anti-biotin antibody for the PRISM® diagnostic analyzer from the current batch range of 30 to 40 mg to a new batch range of 50 to 150 mg to enable the manufacturer to meet future demand, alternative size exclusion chromatography (SEC) columns were evaluated and compared with the Tosoh silica-based column currently in use by the manufacturer 20 (TSK-GEL G3000SW). The Tosoh TSK-GEL G3000SW column is described in TSKgel G3000SW, Tosoh Bioscience LLC, available on the world wide web at the Tosoh Bioscience website.

Three pre-packed, low-pressure size exclusion columns were chosen for evaluation, based on the manufacturer's stated fractionation range for globular proteins of $10^4$ to $10^6$ $M_r$. The columns evaluated exhibited the characteristics listed in TABLE 2.

TABLE 2

| Parameter | Value or range of values |
|---|---|
| Inside diameter | 16 mm |
| Bed height | 600 mm |
| Packing | (a) SEPHACRYL ™ S-200 HR, (b) SEPHACRYL ™ S-300 HR, or (b) HILOAD ™ 16/60 SUPERDEX ™ 200 pg (all columns were provided by Amersham Biosciences/GE Healthcare). |

The biological conjugate comprised an anti-biotin antibody moiety and an acridinium moiety. The molar input ratio of the acridinium moiety (330 μL) to the anti-biotin antibody moiety (7.8 mL, 9.6 mg/mL) was 5.1 to 1. A buffer having a pH of 8.0 was used at a volume of 0.78 mL. Each column was loaded with biological conjugate (2.5 mL), which was equivalent to approximately 2.1% of the loading volume of the column, for an initial evaluation. FIG. 4A shows absorbance (left y-axis) and molar incorporation ratio (right y-axis) as a function of fraction number for the purification process. The curve designated by diamonds shows corrected absorbance as a function of fraction number at a wavelength of 280 nm. The curve designated by squares shows calculated absorbance as a function of fraction number at a wavelength of 370 nm. Line A1 represents an incorporation ratio of acridinium to anti-biotin antibody of 2.5. Line A2 represents an incorporation ratio of acridinium to anti-biotin antibody of 1.3. FIG. 4B shows absorbance (left y-axis) and molar incorporation ratio (right y-axis) as a function of fraction number for the purification process. The curve designated by diamonds shows corrected absorbance as a function of fraction number at a wavelength of 280 nm. The curve designated by squares shows calculated absorbance as a function of fraction number at a wavelength of 370 nm. Line A1 represents an incorporation ratio of acridinium to anti-biotin antibody of 2.5. Line A2 represents an incorporation ratio of acridinium to anti-biotin antibody of 1.3. FIG. 4C shows absorbance (left y-axis) and molar incorporation ratio (right y-axis) as a function of fraction number for the purification process. The curve designated by diamonds shows corrected absorbance as a function of fraction number at a wavelength of 280 nm. The curve designated by squares shows calculated absorbance as a function of fraction number at a wavelength of 370 nm. Line A1 represents an incorporation ratio of acridinium to anti-biotin antibody of 2.5. Line A2 represents an incorporation ratio of acridinium to anti-biotin antibody of 1.3.

The portions of the resulting chromatograms showing the separation of the biological conjugate (main peak) from the aggregate (small peaks immediately preceding the main peak) are shown in FIGS. 4D, 4E, and 4F. The main objective of the step for purifying the biological conjugate is to remove the un-reacted free acridinium from the biological conjugate. All three columns evaluated in EXAMPLE 1 easily achieved this objective. The un-reacted, free acridinium component was well-resolved from the peak of the biological conjugate. The acridinium peaks in the chromatograms shown in FIGS. 4D, 4E, and 4F are present at a retention time of 106, 105, and 113 minutes, respectively. The SEPHACRYL™ S-200 HR and the SEPHACRYL™ S-300 HR columns resolved one aggregate peak immediately preceding the main peak of the biological conjugate, while the HILOAD™ 16/60 SUPERDEX™ 200 pg column resolved two aggregate peaks immediately preceding the main peak of the biological conjugate. The resolution of the HILOAD™ 16/60 SUPERDEX™ 200 pg column was better than the resolution of the SEPHACRYL™ S-200 HR column. The resolution of the SEPHACRYL™ S-200 HR column was better than the resolution of the SEPHACRYL™ S-300 HR column. The HILOAD™ 16/60 SUPERDEX™ 200 pg column provided the best overall separation characteristics, and was therefore selected for further characterization studies. As used herein, "overall separation characteristics" involves the greatest the degree of separation between the biological conjugate and the aggregate.

Example 2

FIG. 5A shows that the HILOAD™ 16/60 SUPERDEX™ 200 pg column also provided an improved Ac/IgG IR profile relative to that of the aforementioned Tosoh silica-based column.

The Ac/IgG IR curve for a typical biological conjugate, purified on the silica-based column using running conditions specified in the current manufacturing protocol, had a significant positive slope (.about.0.25 incorporation ratio unit per fraction) as it moved from left to right across the main peak of the biological conjugate. See FIG. 5A. The sloping Ac/IgG IR curve is indicative of an interaction between the biological conjugate and the packing material of the column. The packing material is the chromatographic medium through which the reaction mixture is passed to effect separation of the components of the reaction mixture. The packing material of the HILOAD™ 16/60 SUPERDEX™ 200 pg column comprises a gel comprised of agarose and dextran, namely, dextran covalently bound to highly cross-linked agarose. As shown in FIG. 5A, the sloping curve results in a significant number of fractions with Ac/IgG IR values outside of the pooling criteria. Only fractions that fall within the desired range for Ac/IgG IR values are included in the final biological conjugate pool. For biological conjugates purified on the silica-based column, exclusion of fractions from the biological conjugate pool can adversely affect the final yield. In contrast, the Ac/IgG IR curve for the biological conjugate purified on the HILOAD™ 16/60 SUPERDEX™ 200 pg column was only slightly concave, which enabled the majority of the fractions corresponding to the peak of the biological conjugate to be included in the final biological conjugate pool. See FIG. 5B. The Ac/IgG IR values for pooling criteria for the existing biological conjugate containing the anti-biotin antibody range from 1.3 to 2.5, while the Ac/IgG IR values for pooling criteria for the biological conjugate containing the anti-biotin antibody purified by the method described herein range from 1.3 to 2.3. Pooling criteria are based on assay performance rather than on performance of the column.

The particular fractions pooled will also be dependent on the position of the Ac/IgG IR curve across the main peak of the biological conjugate. The biological conjugate pool containing the biological conjugates purified by the HILOAD™ 16/60 SUPERDEX™ 200 pg column will better reflect the average biological conjugate.

Example 3

This example illustrates the range of column loadings attainable by a HILOAD™ 16/60 SUPERDEX™ 200 pg column. A HILOAD™ 16/60 SUPERDEX™ 200 pg column was used to purify a biological conjugate containing anti-biotin antibody over a range of per cents of column loading, up to 15.4%, where percent column loading equals 100% multiplied by the ratio of volume of the sample to volume of the column. The effect of loading volumes on the Ac/IgG IR values and yield of the final biological conjugate, as well as on assay performance, were evaluated to determine an appropriate upper limit for the percent of column loading. The percent of aggregate, i.e., 100% multiplied by the quotient of the area(s) under the aggregate peak(s) divided by the sum of (a) the area(s) under the aggregate peaks(s) and (b) the area under the conjugate peak, was determined for each loading condition in order to evaluate the degree of separation of the biological conjugate from the aggregate. The yields for the final biological conjugate were used to determine the most appropriate size for a column for full-scale production.

In a first protocol, an anti-biotin antibody (7.8 mL, 9.9 mg/mL) was conjugated with N-methyl acridinium (330 µL, 4.33 mg/µL). A conjugation buffer (0.78 mL) having a pH of 8.0 was used. The molar input ratio of acridinium to anti-biotin antibody was 5.1 to 1. The expression "molar input ratio" means the ratio of the number of moles of the label to the number of moles of the specific bonding member. A loading volume of 6 mL represented 5% of the volume of the column. In a second protocol, an anti-biotin antibody (17.7 mL, 9.9 mg/mL) was conjugated with N-methyl acridinium (586 µL, 4.33 mg/µL). A conjugation buffer (1.77 mL) having a pH of 8.0 was used. The molar input ratio of acridinium to anti-biotin antibody was 4.0 to 1. A loading volume of 18.5 mL represented 15.4% of the volume of the column. In a third protocol, an anti-biotin antibody (26 mL, 9.9 mg/mL) was conjugated with N-methyl acridinium (790 µL, 4.33 mg/µL). A conjugation buffer (2.6 mL) having a pH of 8.0 was used. The molar input ratio of acridinium to anti-biotin antibody was 4.14 to 1. A loading volume of 15 mL represented 12.5% of the volume of the column. In a fourth protocol, an anti-biotin antibody (26 mL, 9.9 mg/mL) was conjugated with N-methyl acridinium (790 µL, 4.33 mg/µL). A conjugation buffer (2.6 mL) having a pH of 8.0 was used. The molar input ratio of acridinium to anti-biotin antibody was 4.14 to 1. A loading volume of 12 mL represented 10% of the volume of the column.

The HILOAD™ 16/60 SUPERDEX™ 200 pg column provided the best separation characteristics relative to the other size exclusion chromatography (SEC) columns. The most appropriate column size required to manufacture at the upper batch limit of 150 mg is dependent on the percent of maximum column loading that will provide adequate separation of the biological conjugate from the aggregate. Maximum column loading means 100% multiplied by the ratio of the maximum volume of a sample that can be injected into the column to the total column volume. As noted previously, separation of the biological conjugate from the free acridinium is easily achieved. To determine the value of percent of maximum column loading, a HILOAD™ 16/60 SUPERDEX™ 200 pg column, having a nominal volume ranging from 120 mL to 124 mL, was used to purify a biological conjugate containing an anti-biotin antibody over a range of percent of column loading volumes up to 15.4%. Fractions having Ac/IgG IR values ranging from 1.3 to 2.5 and a minimum reading of 1.0 absorbance unit at a wavelength of 280 nm were pooled. The separations were evaluated by measuring the amount of aggregate in the final biological conjugate pool, as well as by testing the biological conjugates for assay performance.

FIGS. 6A, 6B, 6C, and 6D illustrate the results of this example. In FIGS. 6A, 6B, 6C, and 6D, the left y-axis represents absorbance units at a wavelength of 280 nm, and the right y-axis represents incorporation ratio units; the x-axis represents the fraction number. In FIGS. 6A, 6B, 6C, and 6D, the curves designated by squares show corrected absorbance as a function of fraction number at a wavelength of 280 nm; the curves designated by rectangles show calculated absorbance as a function of fraction number at a wavelength of 370 nm; the curves designated by triangles show the molar incorporation ratio of acridinium to anti-biotin antibody. In FIGS. 6A, 6B, 6C, and 6D, line A1 represents an incorporation ratio (acridinium to anti-biotin-antibody) of 2.5; line A2 represents an incorporation ratio (acridinium to anti-biotin-antibody) of 1.3. The percent of aggregate in the final biological conjugates at various loadings is summarized in TABLE 3, along with the summary of performance of the biological conjugate. The percent aggregate was analyzed by means of a TSK-GEL G3000SW column. Biological conjugates containing up to 1% aggregate exhibited acceptable assay performance relative to the reference biological conjugate, with no trend in the ratio of positive counts to negative counts or in the ratio of signal to cutoff as the column loading increased.

TABLE 3

| Column loading (%) | Aggregate in final pool (%) | Performance of biological conjugate | Yield of biological conjugate (mg) |
|---|---|---|---|
| 5 | 0* | Passed | Not available |
| 10 | 0.0 | Passed | 72.1 (66%) |
| 12.5 | 0.6 | Passed | 99.6 (72%) |
| 15.4 | 1.0 | Passed | 123 (72%) |

*The final pool for the 5% loading was not measured; however, all fractions used to prepare the final pool contained 0% aggregate.

A yield of biological conjugate containing anti-biotin antibody of 123 mg was achieved on the HILOAD™ 16/60 SUPERDEX™ pg column at 15.4% column loading, with low levels of aggregate in the final pool and acceptable assay performance. The data show that a HILOAD™ 26/60 SUPERDEX™ 200 pg column, which has 2.57 to 2.75 times the bed volume of the HILOAD™ 16/60 SUPERDEX™ 200 pg column, can be reliably used to manufacture a biological conjugate at a batch size of 150 mg. Further justification for the upper batch limit is provided below.

The ability of a size exclusion chromatography (SEC) column to separate species, e.g. biological conjugate from aggregate, that have similar eluting times, e.g., within five (5) minutes of each other, will decrease as the percent of column loading is increased. Therefore, it is necessary to establish the maximum value of the percent of column loading that will provide adequate separation of the biological conjugate from the aggregate. Acceptable separation, acceptable Ac/IgG IR values, and acceptable assay performance were obtained at column loadings up to 15.4%.

Example 4

This example illustrates a fully scaled-up purification of a biological conjugate with a HILOAD™ 26/60 SUPERDEX™ 200 column, which had a nominal volume ranging from 319 mL to 330 mL. To maintain the percent of column loading below 15.4% on a HILOAD™ 26/60 SUPERDEX™ pg column, the volume of the biological conjugate must be less than 49.0 mL. Using this value as an upper boundary, the maximum batch size supported by the characterization data was determined to be 225 mg. The upper batch size for actual production runs is expected to be set at about 75 mg below this limit (i.e., 150 mg).

The range of batch sizes for a HILOAD™ 26/60 SUPERDEX™ 200 pg column was set at 50 mg to 150 mg. The minimum batch size was set equal to a column loading of approximately 2%. This loading volume was equal to that used in the selection of the HILOAD™ 26/60 SUPERDEX™ 200 pg column, which provided excellent separation. At the maximum batch size, the highest percent of loading occurred when the anti-biotin antibody was at its lowest concentration of 7.0 mg/mL, and therefore required the greatest volume of the biological conjugate. At a batch size of 150 mg, the maximum percent loading volume was 32.7 mL. This volume was equivalent to a 10.3% loading volume on a HILOAD™ 26/60 SUPERDEX™ 200 pg column, and was approximately two-thirds (66.9%) the maximum column loading shown to be effective. A fully scaled-up, maximum batch size run was successfully completed on a HILOAD™ 26/60 SUPERDEX™ 200 pg column. Yields of biological conjugates, Ac/IgG IR values, and assay performance were acceptable over the range of batch sizes.

Example 5

This example illustrates the purification of a series of biological conjugates on a single column. A total of fourteen (14) biological conjugates containing anti-biotin antibody and acridinium label for a PRISM® automated analyzer were prepared on a single HILOAD™ 16/60 SUPERDEX™ 200 pg column (Amersham Code 17-1069-01, ID No. 0433030, Lot 304941). A diminution in assay performance from biological conjugate to biological conjugate was not apparent. Performance of the column was based on the separation of the biological conjugate from both free acridinium and the aggregate. The column was flushed with two (2) to three (3) bed volumes of 1% sodium azide either between runs or before storage. The HILOAD™ 16/60 SUPERDEX™ 200 pg column was subjected to more than one (1) column volume of air between the eleventh and twelfth purification runs for the biological conjugate. Nevertheless, subsequent purification runs (runs 12, 13, and 14) continued to exhibit acceptable separation of the biological conjugate from both free acridinium and the aggregate.

Example 6

This example illustrates how the clean-in-place procedure recommended by the manufacturer maintains the effectiveness of the column between purifications of biological conjugate. The column was washed with 0.5 M NaOH, according to the manufacturer's recommended procedure. The instructions for the HILOAD™ 16/60 SUPERDEX™ 200 pg column and for the for the HILOAD™ 26/60 SUPERDEX™ 200 pg column are set forth in GE Healthcare, Instructions 71-5020-20AF High Performance Columns, HILOAD™ 16/60 and 26/60 SUPERDEX™ 30 prep grade, HILOAD™ 16/60 and 26/60 SUPERDEX™ 75 prep grade, HILOAD™ 16/60 and 26/60 SUPERDEX™ 200 prep grade, General Electric Company 2005, previously incorporated herein by reference. Several small peaks resulted from elution from the column during the clean-in-place procedure and during the subsequent equilibration with phosphate buffered saline. The presence of peaks indicated that the use of 0.5 N NaOH removed non-specifically absorbed material from the column. The relative amount of material that was washed off the column during the cleaning procedure was low (i.e., the number of absorbance units generated was low), even after 14 preparations of biological conjugate in the absence of previous column cleaning by NaOH. The maximum absorbance generated by the material eluted from the column was less than 0.15 absorbance unit (at a wavelength of 280 nm). Maximum peak values at a wavelength of 280 nm for characterization runs for purification of the biological conjugate were approximately 7 to 9 absorbance units.

The pH of the phosphate buffered saline buffer used to re-equilibrate the column was also measured to determine an appropriate volume of wash liquid before storage of the column. FIG. 7 shows that the column eluent returned to neutral pH after 1.5 column volumes of washing liquid and the absorbance at a wavelength of 280 nm returned to a stable baseline within 1.6 column volumes of washing liquid. The upper dashed line represents the pH of 0.5 N NaOH (13.7), while the lower dashed line represents the pH of the phosphate buffered saline (7.0).

Example 7

This example illustrates whether the method described herein maintains lot-to-lot stability in a given column. A HILOAD™ 16/60 SUPERDEX™ 200 pg column (Amersham Code 17-1069-01, ID No. 0433030, Lot 307374) was used to prepare thirteen (13) biological conjugates containing anti-biotin antibody to demonstrate the stability of the column from lot-to-lot, as well as to verify that there is no adverse effect on performance of the column and performance of the biological conjugate in assays resulting from repeated clean-in-place procedures. Again, as previously seen in EXAMPLE 5, the column exhibited acceptable separation characteristics over the course of thirteen runs. In addition, the number of theoretical plates and operating pressure at a rate of 1.0 mL/min (nominal setting) were recorded. FIG. 8 shows that the values were stable, thereby indicating that performance of the column was highly reproducible and stable. All thirteen biological conjugates exhibited HIV-0+assay performance comparable to the existing reference biological conjugate. The data in FIG. 8 demonstrate that HILOAD™ 16/60 SUPERDEX™ 200 pg columns can be used to successfully manufacture as many as thirteen biological conjugates containing anti-biotin antibody when utilizing the clean-in-place procedure recommended by the manufacturer. The number of runs for a single HILOAD™ 16/60 SUPERDEX™ 200 pg column or a HILOAD™ 26/60 SUPERDEX™ 200 pg column is preferably limited to 10 runs.

Example 8

This example illustrates the effect of input ratio on the purification characteristics of a biological conjugate. A series of biological conjugates was prepared over a range of Ac/IgG IR values by varying the input ratio of acridinium to anti-biotin antibody. The input ratio of acridinium to anti-biotin antibody was varied by changing the amount of activated acridinium used in the conjugation reaction, while holding the amount of anti-biotin antibody constant. The input ratio is expressed as microliters of acridinium per milligram of anti-biotin antibody. A single lot of both the activated acridinium and anti-biotin antibody were used to prepare these biological conjugates; therefore, the ratio of the microliters of acridinium to the milligrams of anti-biotin antibody is directly proportional to the molar input ratio. The inputs are summarized in TABLE 4, along with the resulting final Ac/IgG IR values and yields corresponding thereto. The concentration of acridinium was approximately 4 mg/mL.

TABLE 4

| Lot | Volume of activated acridinium (µL) | Weight of anti-biotin antibody (mg) | Initial input ratio (volume of activated acridinium to weight of anti-biotin antibody) | Final incorporation ratio (volume of activated acridinium to weight of anti-biotin antibody) | Yield (mg) |
|---|---|---|---|---|---|
| S-D | 60.6 | 25 | 2.42 | 1.25 | 18.4 (74%) |
| S-A | 76.7 | 25 | 3.07 | 1.65 | 18.9 (76%) |
| S-B | 85 | 25 | 3.40 | 1.82 | 19.8 (79%) |
| S-C | 94.7 | 25 | 3.79 | 2.07 | 18.0 (72%) |

FIG. 9 shows that the final Ac/IgG IR values of the biological conjugates purified on a HILOAD™ 16/60 SUPERDEX™ 200 pg column is highly correlated with the incorporation ratio of acridinium to anti-biotin antibody. The final Ac/IgG IR value increased linearly with increasing Ac/IgG IR values ($R^2$=0.999). In addition, the yields were consistent and independent of the Ac/IgG IR values.

Size exclusion chromatography HPLC analysis of 13 biological conjugates prepared according to the with the process described herein was performed to determine the percent aggregate present in the final samples of biological conjugate, as well as in the two to three fractions preceding the biological conjugate pool. No measurable aggregate peak was present in the final pools from all 13 runs.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for separating a biological conjugate from an aggregate in a mixture produced by manufacturing the biological conjugate, the method comprising the steps of:
    (a) providing a mixture comprising the biological conjugate and the aggregate, wherein the mixture comprises a batch size ranging from about 50 to about 150 mg and the biological conjugate comprises a chemiluminescent label covalently linked to an anti-biotin antibody;
    (b) providing a chromatography column containing a gel, wherein the gel comprises at least one polysaccharide;
    (c) introducing the mixture of step (a) into the chromatography column; and
    (d) recovering the biological conjugate from the column;
    wherein the biological conjugate has a globular structure, the aggregate comprises aggregated protein and aggregated label, and the molecular weight of the aggregate is the same as to double the weight of a single molecule of the biological conjugate.

2. The method of claim 1, wherein the chemiluminescent label comprises acridinium.

3. The method of claim 1, wherein the loading volume of the chromatography column ranges from about 0.2% to about 15.4%.

4. The method of claim 1, wherein the biological conjugate comprises a label and a specific binding member having an input ratio ranging from about 0.5 µL of the label/mg of the specific binding member to about 6 µL of the label/mg of the specific binding member.

5. The method of claim 1, wherein the biological conjugate comprises a label and a specific binding member having an incorporation ratio ranging from about 1.3 to about 2.5.

6. The method of claim 1, wherein the method separates the biological conjugate from the aggregate with a selectivity of at least about 1.8.

7. The method of claim 6, wherein the selectivity ranges from about 1.8 to about 3.6.

8. The method of claim 1, wherein the at least one polysaccharide is dextran.

9. The method of claim 1, wherein the at least one polysaccharide is agarose.

10. The method of claim 1, wherein the at least one polysaccharide comprises dextran and agarose.

11. The method of claim 10, wherein the dextran is covalently bound to highly cross-linked agarose.

12. The method of claim 1, wherein the chemiluminescent label is covalently linked to an amine on the anti-biotin antibody.

13. The method of claim 1, wherein the biological conjugate is an anti-biotin antibody covalently linked to a chemiluminescent label.

\* \* \* \* \*